(12) United States Patent
Sumi et al.

(10) Patent No.: US 8,097,635 B2
(45) Date of Patent: Jan. 17, 2012

(54) INSULIN RESISTANCE IMPROVING AGENT

(75) Inventors: Mika Sumi, Ibaraki (JP); Fumiko Ogino, Ibaraki (JP); Toshikazu Kamiya, Ibaraki (JP); Masahiko Nakano, Niigata (JP); Kazutoshi Kikkawa, Tokyo (JP)

(73) Assignees: Kyowa Hakko Bio Co., Ltd., Tokyo (JP); Mitsubishi Gas Chemical Company, Inc., Tokyo (JP)

( * ) Notice: Subject to any disclaimer, the term of this patent is extended or adjusted under 35 U.S.C. 154(b) by 400 days.

(21) Appl. No.: 12/440,807

(22) PCT Filed: Sep. 19, 2007

(86) PCT No.: PCT/JP2007/068114
§ 371 (c)(1),
(2), (4) Date: Mar. 11, 2009

(87) PCT Pub. No.: WO2008/035686
PCT Pub. Date: Mar. 27, 2008

(65) Prior Publication Data
US 2010/0093780 A1    Apr. 15, 2010

(30) Foreign Application Priority Data
Sep. 19, 2006   (JP) ................. 2006-253265

(51) Int. Cl.
*A61K 31/44*    (2006.01)
(52) U.S. Cl. ......... 514/287; 514/292; 514/293; 514/866
(58) Field of Classification Search ............. 514/287, 514/292, 293, 866
See application file for complete search history.

(56) References Cited

U.S. PATENT DOCUMENTS

| 4,898,870 A * | 2/1990 | Narutomi et al. ............. 514/292 |
| 5,369,112 A | 11/1994 | Maeda et al. |
| 7,241,461 B2 | 7/2007 | Myhill et al. |
| 2002/0106404 A1 | 8/2002 | Lipton |
| 2007/0259908 A1 * | 11/2007 | Fujii et al. ................ 514/292 |

FOREIGN PATENT DOCUMENTS

| JP | 61-058584 | 3/1986 |
| JP | 63-41421 | 2/1988 |
| JP | 63-48215 | 2/1988 |
| JP | 63-156724 | 6/1988 |
| JP | 04-198128 | 7/1992 |
| JP | 05-078247 | 3/1993 |
| JP | 06-211660 | 8/1994 |
| JP | 06-256191 | 9/1994 |
| JP | 08-020512 | 1/1996 |
| JP | 08-020585 | 1/1996 |
| JP | 3625493 | 1/1996 |
| JP | 10-025292 | 1/1998 |
| JP | 2001-518096 | 10/2001 |
| WO | 98/43621 | 10/1998 |
| WO | 2005/094862 | 10/2005 |
| WO | 2006/025247 | 3/2006 |
| WO | WO 2007105730 A1 * | 9/2007 |
| WO | 2007/130509 | 11/2007 |

OTHER PUBLICATIONS

Kumazawa, et al., "Trace levels of pyrroloquinoline quinone in human and rat samples detected by gas chromatography/mass spectrometry", Biochimica et Biophysica Acta, vol. 1156 (1992) 62-6.
Kumazawa, et al., "Levels of pyrroloquinoline quinone in various foods", Biochemical Journal, vol. 307 (1995) 331-33.
Salisbury, et al., "A novel coenzyme from bacterial primary alcohol dehydrogenases", Nature, vol. 280 (1979) 843-44.
Duine, et al., "Glucose Dehydrogenase from *Acinetobacter calcoaceticus* (A 'quinoprotein')", FEBS Letters, vol. 108, No. 2 (1979) 443-6.
Yajima, et al., "Combination therapy with PPARγ and PPARα agonists increases glucose-stimulated insulin secretion in db/db mice", Am J Physiol Endocrinol Metab, vol. 284 (2003) E966-71.
Araki, et al., "Oxidative Stress and Insulin Resistance", Annual Review Diabetes-Metabolism-Endocrine (2006) 5-13.
McInerney, et al., "Effects of a 33 residue interleukin-1B Peptide and the Antioxidant PQQ on Interleukin-1B—Mediated Inhibition of Glucose-Stimulated Insulin Release From Cultured Mouse Pancreatic Islets", Research Communications in Molecular Pathology and Pharmacology, vol. 94, No. 2 (1996) 115-28.
Ando, "Oxidative Stress", Japanese Journal of Clinical Medicine, vol. 61, No. 7 (2003) 1130-37.

\* cited by examiner

*Primary Examiner* — Kevin E Weddington
(74) *Attorney, Agent, or Firm* — Fitzpatrick, Cella, Harper & Scinto

(57) ABSTRACT

An object of the present invention is to provide a safe and highly effective insulin resistance improving agent or therapeutic agent for type II diabetes. According to the present invention, an insulin resistance improving agent or a therapeutic agent for type II diabetes comprising a compound represented by general formula (I)

(I)

[Chemical structure: a tricyclic pyrroloquinoline quinone-type compound with substituents $R_1OOC$-, $R_2OOC$-, $R_3OOC$-, HN, and two C=O groups]

(wherein $R_1$, $R_2$, and $R_3$ are the same as or different from each other, and each represents lower alkyl, lower alkenyl, lower alkynyl, aralkyl, araryl, phenyl, or a hydrogen atom) or a salt thereof as an active ingredient can be provided.

2 Claims, No Drawings

INSULIN RESISTANCE IMPROVING AGENT

TECHNICAL FIELD

The present invention relates to an insulin resistance improving agent or a therapeutic agent for type II diabetes comprising pyrroloquinoline quinone, an ester thereof, or a salt thereof as an active ingredient.

BACKGROUND ART

Pyrroloquinoline quinone (hereinafter referred to as "PQQ") was discovered in 1979 as a coenzyme of methanol dehydrogenase in methanol assimilating microorganisms (see "Nature," 1979, Vol. 280, pp. 843-844; and "FEBS Letters," 1979, Vol. 108, pp. 443-446). Other than such microorganisms, PQQ has also been detected in edible plants such as soybean, horse bean, green pepper, potato, parsley, and spinach and processed foods such as vinegar, tea, cocoa, natto, and tofu (see "Biochemical Journal," 1995, Vol. 307, pp. 331-333). Furthermore, the presence of PQQ in humans and rats in vivo has been reported (see "Biochimica et Biophysica Acta," 1992, Vol. 1156, pp. 62-66). PQQ is a highly safe substance.

Known effects of PQQ are as follows: a cell growth promoting effect (see JP Patent Publication (Kokai) No. 61-58584 A (1986)), an active oxygen eliminating effect (see JP Patent Publication (Kokai) No. 5-078247 A (1993)), an aldose reductase-inhibiting effect (see JP Patent Publication (Kokai) No. 6-256191 A (1994)), a nerve growth factor production promoting effect (see JP Patent Publication (Kokai) No. 6-211660 A (1994)), a reverse transcriptase inhibiting effect (see JP Patent Publication (Kokoku) No. 8-005792 B (1996)), an anti-cataract effect (see JP Patent Publication (Kokoku) No. 8-005791 B (1996)), melanin production suppressing and skin lightening effects (see JP Patent Publication (Kokai) No. 8-020512 A (1996)), and an ultraviolet absorption effect (see JP Patent No. 3625493), for example.

Meanwhile, medicaments for improvement of insulin resistance are thought to be useful as prophylactic and therapeutic drugs for lifestyle-related diseases such as diabetes, arteriosclerosis, and hyperlipemia. In particular, type II diabetes is a disease that is developed mainly due to lowered insulin action (insulin resistance) in target tissues of insulin, including skeletal muscle, liver, and adipose tissue. The insulin resistance improving agent is effective as a therapeutic drug for such type II diabetes. Based on their mechanisms of action, therapeutic agents for diabetes are classified as sulfonylurea agents, prompt and short acting agents for accelerating insulin secretion, α-glucosidase inhibitors, biguanides, or thiazolidin derivatives. These therapeutic agents are used independently or in combinations for the treatment of diabetes. Of these therapeutic agents, thiazolidine-based therapeutic agents, which are general insulin resistance improving agents, are known to cause body weight gain as a side effect (see "American Journal Physiology Endocrinology Metabolism" 2003, Vol. 284, pp. 966-971). Therefore, it has been desired to develop an insulin resistance improving agent that would have mild side effects and would be highly safe.

DISCLOSURE OF THE INVENTION

Problems to be Solved by the Invention

An object of the present invention is to provide an insulin resistance improving agent or a therapeutic agent for type II diabetes.

Means to Solve the Problems

The present invention provides an insulin resistance improving agent and a therapeutic agent for type II diabetes as in the following (1) to (6).

(1) An insulin resistance improving agent, which comprises a compound [hereinafter, referred to as compound (I)] represented by general formula (I)

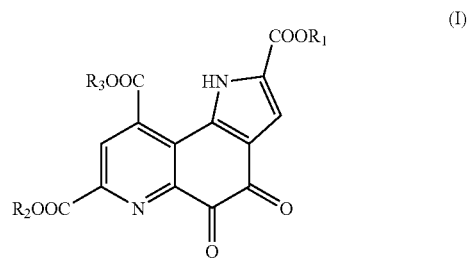

(wherein $R_1$, $R_2$, and $R_3$ are the same as or different from each other, and each represents lower alkyl, lower alkenyl, lower alkynyl, aralkyl, araryl, phenyl, or a hydrogen atom) or a salt thereof as an active ingredient.

(2) A method for improving insulin resistance, which comprises administering an effective amount of the compound represented by general formula (I) according to (1) above or a salt thereof to a subject in need thereof.

(3) Use of the compound represented by general formula (I) according to (1) above or a salt thereof for the manufacture of an insulin resistance improving agent.

(4) A therapeutic agent for type II diabetes, which comprises the compound represented by general formula (I) according to (1) above or a salt thereof as an active ingredient.

(5) A method for treating type II diabetes, which comprises administering an effective amount of the compound represented by general formula (I) according to (1) above or a salt thereof to a subject in need thereof.

(6) Use of the compound represented by general formula (I) according to (1) above or a salt thereof for the manufacture of a therapeutic agent for type II diabetes.

Effect of the Invention

According to the present invention, an insulin resistance improving agent or a therapeutic agent for type II diabetes containing PQQ or an ester thereof, or a salt thereof as an active ingredient can be provided.

This description includes part or all of the contents as disclosed in the description and/or drawings of Japanese Patent Application No. 2006-253265, which is the priority application of the present application.

BEST MODE FOR CARRYING OUT THE INVENTION

According to the definition for compound (I), in the formula, $R_1$, $R_2$, and $R_3$ are the same as or different from each other, and each represents lower alkyl, lower alkenyl, lower alkynyl, aralkyl, araryl (alkyl aryl), phenyl, or a hydrogen atom. Examples of such lower alkyl and alkyl portions of aralkyl and araryl include linear or branched C1-6 alkyl, and more specific examples thereof include methyl, ethyl, propyl, isopropyl, butyl, sec-butyl, tert-butyl, pentyl, isopentyl, neopentyl, and hexyl. In particular, methyl or ethyl is preferable.

Examples of lower alkenyl include linear or branched C2-6 alkenyl and more specific examples thereof include vinyl, allyl, 1-propenyl methacryl, crotyl, 1-butenyl, 3-butenyl, 2-pentenyl, 4-pentenyl, 2-hexenyl, and 5-hexenyl.

Examples of lower alkynyl include linear or branched C2-6 alkynyl and more specific examples thereof include ethynyl, propynyl, butynyl, pentinyl, and hexynyl.

Examples of aralkyl include C7-15 aralkyl and more specific examples thereof include benzyl, phenethyl, benzhydryl, and naphthylmethyl.

Examples of an aryl portion of araryl include C6-14 aryl and more specific examples thereof include phenyl, naphthyl, and anthryl. Accordingly, examples of araryl include methyl phenyl and ethyl phenyl.

PQQ (that is, a compound represented by general formula (I) above wherein $R_1$, $R_2$, and $R_3$ are all hydrogen atoms) can be produced by an organic chemical method (e.g., J. Am. Chem. Soc., 103, 5599-5600 (1981)) and a fermentation method. For example, PQQ can be produced by a method for producing pyrroloquinoline quinone (JP Patent Publication (Kokai) No. 1-218597 A (1989)), which comprises culturing a bacterium capable of assimilating methanol and producing pyrroloquinoline quinone in a culture medium comprising methanol as a carbon source in which the concentration of an iron compound is controlled.

Regarding a method for producing an ester body of PQQ represented by compound (I), such ester body can be synthesized from PQQ via an esterification reaction according to a conventional method.

A triester body of PQQ can be easily synthesized by a method that involves reacting PQQ or a salt thereof with alcohols under acidic conditions (e.g., JP Patent Publication (Kokai) No. 3-123781 A (1991) and JP Patent Publication (Kokai) No. 3-145492 A (1991)) or a method that involves reacting PQQ or a salt thereof with an alkyl halide, an alkenyl halide, an alkynyl halide, an aralkyl halide, an araryl halide, or the like in the presence of a base, for example. Moreover, the triester body of PQQ obtained by the above methods is partially hydrolyzed under acidic or basic conditions, so that a monoester body or a diester body can be obtained.

The thus obtained compound (I) can be separated and purified from a reaction solution by a general method such as column chromatography, recrystallization, and solvent extraction. Moreover, various means are employed for identification of the compound (I), such as elementary analysis, NMR spectrum, IR spectrum, and mass spectroscopy.

Examples of a salt of the compound (I) include alkali metal salts such as a sodium salt and a potassium salt, alkaline-earth metal salts such as a magnesium salt and a calcium salt, organic amine salts such as ammonium, triethanolamine, and triethylamine, and basic amino acid salts such as lysine and arginine.

The insulin resistance improving agent or the therapeutic agent for type II diabetes of the present invention can be a formulation comprising the compound (I) or a salt thereof alone, a formulation comprising a mixture thereof, or a formulation comprising a mixture of the compound (I) or a salt thereof with active ingredients for other arbitrary therapies. Such formulation is produced by mixing active ingredients with one or more types of pharmacologically acceptable carrier according to any method known in the technical field of galenical pharmacy.

The route of administration of the formulation that is the most effective for treatment is desirably used. Examples of such route of administration include oral administration and parenteral administration such as intravenous, intraperitoneal, or intradermal administration. Oral administration is preferable herein.

Examples of dosage forms that may be used for administration include: oral preparations such as tablets, powders, fine granules, pills, suspensions, emulsions, infusions, decoctions, capsules, syrups, liquids, elixirs, extracts, tinctura, and fluid extracts; and parenteral preparations such as injections, infusions, creams, and suppositories. In particular, oral preparations are adequately used.

Upon formulation of an oral preparation, an additive such as an excipient, a binder, a disintegrating agent, a lubricant, a dispersant, a suspension, an emulsifier, a diluent, a buffering agent, an antioxidant, or a microbial inhibitor can be used.

Furthermore, tablets, powders, fine granules, or the like, which are appropriate for oral administration, for example, can be formulated by adding: a saccharide such as lactose, glucose, sucrose, mannitol, and sorbitol; starch such as potato, wheat, and corn; a mineral such as calcium carbonate, calcium sulfate, sodium hydrogencarbonate, and sodium chloride; an excipient such as crystalline cellulose and powdered plants (e.g., powdered glycyrrhiza, and powdered gentian); a disintegrating agent such as starch, agar, gelatin powder, crystalline cellulose, carmellose sodium, carmellose calcium, calcium carbonate, sodium hydrogencarbonate, and sodium alginate; a lubricant such as magnesium stearate, talc, hydrogenated vegetable oil, Macrogol, and silicone oil; a binder such as polyvinyl alcohol, hydroxypropyl cellulose, methyl cellulose, ethyl cellulose, carmellose, gelatin, and a starch paste solution; a surfactant such as a fatty acid ester; and a plasticizer such as glycerin, for example.

When the dosage form is a liquid preparation such as a syrup, formulation can be carried out by adding water, saccharides such as sucrose, sorbitol, and fructose, glycols such as polyethylene glycol and propylene glycol, oils such as sesame oil, olive oil, and soybean oil, antiseptics such as p-hydroxybenzoic acid esters, paraoxybenzoate derivatives such as methyl parahydroxybenzoate, preservatives such as sodium benzoate, flavors such as a strawberry flavor and peppermint, and the like.

Moreover, additives that are generally used for foods or beverages may be added to formulations appropriate for oral administration. Examples of such additives include sweet-tasting substances, coloring agents, preservatives, thickening and stabilizing agents, antioxidants, color formers, bleaching agents, fungicides, gum bases, bitter-tasting substances, enzymes, brighteners, acidifiers, seasonings, emulsifiers, fortifier dietary supplements, additives for production, perfumes, and spice extracts. Formulations appropriate for oral administration may be directly used or used in the form of powdered foods, sheet-shaped foods, bottled foods, canned foods, retort-packed foods, capsulated foods, tablet foods, liquid foods, drinkable preparations, or the like as foods or beverages such as health foods, functional foods, nutritional supplements, or specified health foods for improvement of insulin resistance or ameliorating hyperinsulinemia.

For example, an injection appropriate for parenteral administration comprises a sterile aqueous agent that is preferably isotonic with the blood of a recipient and comprises the compound (I) or a salt thereof. For example, in the case of such injection, a solution for injection is prepared using a carrier or the like comprising a salt solution, a glucose solution, or a mixture of a salt solution and a glucose solution.

Furthermore, to these parenteral preparations, one or more types of auxiliary ingredient selected from among the aforementioned examples of oral preparations, such as diluents, antiseptics, flavors, excipients, disintegrating agents, lubricants, binders, surfactants, plasticizers, and the like can be added.

The concentration of the compound (I) or a salt thereof in the formulation of the present invention is adequately selected depending on the type of formulation, effects expected to be exerted as a result of administration of the formulation, and the like. For example, in the case of oral preparations, the concentration of the compound (I) or a salt thereof generally ranges from 0.1% to 100% by weight, preferably ranges from 0.5% to 70% by weight, and particularly preferably ranges from 1% to 50% by weight.

The dose and the frequency of administration of the formulation of the present invention differ depending on the route of administration, age and body weight of a patient, and characteristics or severity of symptoms to be treated. In general, the compound (I) or a salt thereof is administered once a day or several separate times a day for an adult so that the dose generally ranges from 0.5 mg to 10000 mg, preferably ranges from 0.5 mg to 5000 mg, and more preferably ranges from 5 mg to 1000 mg per day for an adult.

The period of administration is not particularly limited. It generally ranges from 1 day to 1 year and preferably ranges from 2 weeks to 3 months.

In addition, the formulation of the present invention can be used not only for humans, but also for animals other than humans (hereinafter, abbreviated as "non-human animal(s)"). Examples of non-human animals include animals other than humans, such as mammals, birds, reptiles, amphibians, and fishes.

The dose for administration to a non-human animal differs depending on the age and the type of the animal and the characteristics or severity of symptoms. In general, the compound (I) or a salt thereof is administered once a day or several separate times a day so that the dose generally ranges from 0.01 mg to 200 mg, preferably ranges from 0.1 mg to 100 mg, and more preferably ranges from 1 mg to 20 mg per kg of body weight per day.

The period of administration is not particularly limited. It generally ranges from 1 day to 1 year and preferably ranges from 2 weeks to 3 months.

EXAMPLES

Hereinafter, test examples are provided. Such tests were used to examine the effect of compound (I) to improve insulin resistance and the therapeutic effect of compound (I) on type II diabetes.

Test Example 1

Twenty seven (27) BKS. Cg-+Lepr$^{db}$/+Lepr$^{db}$/JcI mice (Clea Japan Inc., female, 7 week old), which were type II diabetes model mice expressing the symptoms of hyperinsulinemia due to insulin resistance, were divided into 3 groups each consisting of 9 mice. The groups were designated as group 1, group 2, and group 3.

Mice of the groups 1 to 3 were fed with free access to pellets CE-2 (Clea Japan Inc.; hereinafter referred to as "CE-2") for feeding mice and rats. To the mice of group 1, 0.5 w/v % methyl cellulose (0.5 w/v % methyl cellulose 400 cP solution, sterilized, produced by Wako Pure Chemical Industries, Ltd. for biochemistry; hereinafter referred to as "0.5% MC") was administered orally once a day (10 mL/kg). To the mice of group 2, a pyrroloquinoline quinone disodium salt (hereinafter referred to as "PQQ disodium salt," produced by Mitsubishi Gas Chemical Company, Inc.) suspended in 0.5% MC to a concentration of 0.5 mg/mL was administered orally once a day (10 mL/kg). To the mice of group 3, a PQQ disodium salt suspended in 0.5% MC to a concentration of 2 mg/mL was administered orally once a day (10 mL/kg).

Table 1 shows the results of changes in body weight on the day on which the test was initiated (day 0) and the day before completion of the test (day 31).

TABLE 1

| | Body weight (g) | |
|---|---|---|
| | Day 0 | Day 31 |
| Group 1 | 29.41 ± 0.20 | 37.30 ± 0.90 |
| Group 2 | 29.90 ± 0.37 | 37.18 ± 0.65 |
| Group 3 | 29.93 ± 0.51 | 39.01 ± 1.07 |

As is clear from Table 1, the body weights of the mice of groups 2 and 3 were almost the same as those of group 1 after completion of the test.

Blood was collected from the orbital veins on day 14 and day 28 after the initiation of the test, and thus serum was obtained. Nonfasting blood serum glucose levels and nonfasting serum insulin concentrations were separately measured using a glucose C-II Test Wako (produced by Wako Pure Chemical Industries, Ltd.) and a Mouse Insulin ELISA Kit (S-type) (produced by Shibayagi Co., Ltd.), respectively. After 18 hours of fasting from day 28 to day 29 after the initiation of the test, a 40% (w/v) glucose aqueous solution was administered orally to each mouse at 2 g/kg B.W., so as to load the mice with glucose (to test the glucose tolerance). Blood was collected from tail veins at the time of administration of a glucose aqueous solution (0 minute) and then at a certain time point after administration (120 minutes). Blood glucose levels were measured using a Medisafe Reader GR-101 (produced by Terumo Corporation). After 18 hours of fasting from day 31 to day 32 after initiation of the test, exsanguination was carried out via the inferior vena cava to obtain serum. Blood serum glucose levels and serum insulin concentrations were separately measured using a glucose C-II Test Wako and a Mouse Insulin ELISA Kit (S-type), respectively. The results were expressed as average levels±standard deviation (n=9). Statistical significance levels (p-values) were found by a t-test (group 1 with respect to group 2; and group 1 with respect to group 3).

Table 2 shows the results of measuring non-fasting blood glucose levels on day 14 and day 28 after initiation of the test.

TABLE 2

| | Blood glucose level (mg/dl) | |
|---|---|---|
| | Day 14 after initiation of test | Day 28 after initiation of test |
| Group 1 | 429.0 ± 11.4 | 594.9 ± 40.4 |
| Group 2 | 427.7 ± 11.4 | 531.5 ± 12.3 |
| Group 3 | 405.7 ± 24.1 | 546.1 ± 26.0 |

As is clear from Table 2, blood glucose levels of group 2 and group 3 on day 14 and day 28 after initiation of the test were lower than those of group 1 on the same dates.

Table 3 shows the results of measuring serum insulin concentrations on day 14 and day 28 after initiation of the test.

TABLE 3

| | Serum insulin concentration (ng/dl) | |
|---|---|---|
| | Day 14 after initiation of test | Day 28 after initiation of test |
| Group 1 | 7.45 ± 2.62 | 5.27 ± 1.34 |
| Group 2 | 4.02 ± 0.75 | 3.02 ± 0.47 |
| Group 3 | 6.23 ± 1.69 | 4.82 ± 1.81 |

As is clear from Table 3, serum insulin concentrations of group 2 and group 3 on day 14 and 28 after initiation of the test were lower than those of group 1 on the same dates.

Table 4 shows the results of the glucose tolerance test.

TABLE 4

| | Blood glucose level (mg/dl) | |
|---|---|---|
| | 0 minute | 120 minutes |
| Group 1 | 320.0 ± 27.1 | 546.4 ± 32.2 |
| Group 2 | 281.3 ± 16.3 | 522.0 ± 22.9 |
| Group 3 | 303.4 ± 25.9 | 489.3 ± 47.5 |

As is clear from Table 4, at 120 minutes after administration of a glucose aqueous solution, blood glucose levels of group 2 and group 3 were lower than those of group 1, suggesting that increases in blood glucose levels resulting from the load of glucose were suppressed.

Table 5 shows the results of measuring fasting blood glucose levels on day 32 after initiation of the test.

TABLE 5

| | Blood glucose level (mg/dl) |
|---|---|
| Group 1 | 688.4 ± 38.0 |
| Group 2 | 617.7 ± 39.1 |
| Group 3 | 575.6 ± 33.3* |

(*$p < 0.05$, with respect to group 1)

As is clear from Table 5, the blood glucose levels of group 3 were significantly lower than those of group 1 on the same date. Moreover, the blood glucose levels of group 2 were lower than those of group 1 on the same date.

Table 6 shows the results of measuring insulin concentrations on day 32 after initiation of the test.

TABLE 6

| | Insulin concentration (ng/dl) |
|---|---|
| Group 1 | 5.17 ± 1.54 |
| Group 2 | 4.88 ± 0.75 |
| Group 3 | 4.40 ± 0.66 |

As is clear from Table 6, the serum insulin concentrations of group 2 and group 3 were lower than those of group 1 on the same date.

The above results revealed that the PQQ disodium salt exerts an effect of improving insulin resistance and a therapeutic effect on type II diabetes without body weight gain.

Test Example 2

Eighteen type II diabetes model KK-AY/Ta JcI mice (Clea Japan Inc., male, 6 week old) were divided into 3 groups (6 mice in group 1, 7 mice in group 2, and 5 mice in group 3). The groups were designated as group 1, group 2, and group 3, respectively.

Mice of the groups 1 to 3 were fed with free access to pellets CE-2 for feeding mice and rats. To the mice of group 1, 0.5% MC was administered orally once a day (10 mL/kg). To the mice of group 2, a PQQ disodium salt suspended in 0.5% MC to a concentration of 0.5 mg/mL was administered orally once a day (10 mL/kg). To the mice of group 3, a PQQ disodium salt suspended in 0.5% MC to a concentration of 2 mg/mL was administered orally once a day (10 mL/kg).

After 18 hours of fasting from day 14 to day 15 after the initiation of the test, a 10% (w/v) glucose aqueous solution was administered orally to each mouse at 1 g/kg B.W., so as to load the mice with glucose to test the glucose tolerance. Blood was collected from tail veins at 0 minutes, 30 minutes, 60 minutes, and 120 minutes after administration of the glucose aqueous solution. Blood glucose levels were measured using a Medisafe Reader GR-101 (produced by Terumo Corporation). Table 7 shows the results. Blood glucose levels were expressed as average levels±standard deviation (n=5-7) and statistical significance levels (p-values) were found by a t-test (group 1 with respect to group 2; and group 1 with respect to group 3).

TABLE 7

| | Blood glucose level (mg/dl) | | | |
|---|---|---|---|---|
| | 0 minutes | 30 minutes | 60 minutes | 120 minutes |
| Group 1 | 125.7 ± 13.8 | 340.3 ± 10.8 | 318.5 ± 16.7 | 231.8 ± 10.2 |
| Group 2 | 116.7 ± 10.1 | 274.9 ± 8.4*** | 264.6 ± 7.6* | 184.3 ± 7.8** |
| Group 3 | 117.0 ± 12.2 | 300.0 ± 24.1 | 261.6 ± 25.6 | 187.4 ± 20.3 |

(*$p < 0.05$,
**$p < 0.01$,
***$p < 0.001$, with respect to group 1)

As is clear from Table 7, blood glucose levels of group 2 measured at 30 minutes, 60 minutes, and 120 minutes after administration of glucose were significantly lower than those of group 1. In group 2, increases in blood glucose level resulting from the load of glucose were suppressed. Moreover, blood glucose levels of group 3 measured at 30 minutes, 60 minutes, and 120 minutes after administration of glucose were lower than those of group 1. Also in group 3, increases in blood glucose level resulting from the load of glucose were suppressed.

The above results revealed that the PQQ disodium salt exerts a therapeutic effect on type II diabetes and also in cases of type II diabetes model mice having a gene mutation differing from that in test example 1.

Next, the present invention will be described in more detail with reference to the following examples relating to the composition according to the present invention, but the invention is not limited thereto.

Example 1

Water is added to the composition shown in Table 8 to 1000 mL, so that soft drinks (10 bottles) for improving insulin resistance are prepared.

TABLE 8

| Composition | Content |
|---|---|
| PQQ disodium salt | 100 mg |
| Vitamin C | 1 g |
| Vitamin B1 | 5 mg |
| Vitamin B2 | 10 mg |
| Vitamin B6 | 25 mg |

TABLE 8-continued

| Composition | Content |
|---|---|
| Liquid sugar | 150 g |
| Citric acid | 3 g |
| Perfume | 1 g |

Example 2

The composition described in Table 9 is extracted with 1000 mL of water, and thus 1000 mL of a tea drink for treatment of type II diabetes is prepared.

TABLE 9

| Composition | Content |
|---|---|
| PQQ dimethyl ester | 100 mg |
| Tea leaf | 15 g |

Example 3

Chewing gum (30 sticks) for improving insulin resistance is prepared from the use of the composition described in Table 10.

TABLE 10

| Composition | Content |
|---|---|
| PQQ trimethyl ester | 100 mg |
| Gum base | 25 g |
| Sugar | 63 g |
| Starch syrup | 10 g |
| Perfume | 1 g |

Example 4

Candies (20 candies) for treatment of type II diabetes are prepared from the composition described in Table 11.

TABLE 11

| Composition | Content |
|---|---|
| PQQ disodium salt | 100 mg |
| Sugar | 80 g |
| Starch syrup | 20 g |
| Perfume | 0.1 g |

Example 5

Tablets (155 mg per tablet) for improving insulin resistance are prepared by a conventional method according to the formulation described in Table 12.

TABLE 12

| Composition | Content |
|---|---|
| PQQ disodium salt | 5 mg |
| Lactose | 90 mg |
| Corn starch | 30 mg |
| Synthetic aluminium silicate | 12 mg |
| Carboxymethylcellulose•calcium | 15 mg |
| Magnesium stearate | 3 mg |

Example 6

Powders (505 mg per package) for treatment of type II diabetes are prepared by a conventional method according to the formulation described in Table 13.

TABLE 13

| Composition | Content |
|---|---|
| PQQ diethyl ester | 5 mg |
| Lactose | 300 mg |
| Corn starch | 200 mg |

Example 7

Hard capsules (115 mg per capsule) for improving insulin resistance are prepared according to the formulation described in Table 14.

TABLE 14

| Composition | Content |
|---|---|
| PQQ monoallyl ester | 5 mg |
| Lactose | 60 mg |
| Corn starch | 30 mg |
| Hydroxypropyl cellulose | 20 mg |

Lactose (60 mg) and corn starch (30 mg) are added to and mixed with 5 mg of PQQ monoallyl ester. An aqueous solution containing 20 mg of hydroxypropyl cellulose is added to the mixture and then kneaded. Subsequently, granules are prepared by a conventional method using an extruding and granulating machine. Hard gelatin capsules are filled with the granules, and thus hard capsules are prepared.

Example 8

Soft capsules (125 mg per capsule) for treatment of type II diabetes are prepared according to the formulation described in Table 15.

TABLE 15

| Composition | Content |
|---|---|
| PQQ disodium salt | 5 mg |
| Soybean oil | 120 mg |

PQQ disodium salt (5 mg) is added to and mixed with 120 mg of soybean oil. Subsequently, soft capsules are filled with the mixture by a conventional method using a rotary soybean automatic molding machine, and thus soft capsules are prepared.

INDUSTRIAL APPLICABILITY

According to the present invention, an insulin resistance improving agent or a therapeutic agent for type II diabetes containing PQQ or an ester thereof, or a salt thereof as an active ingredient can be provided.

All publications, patents, and patent applications cited in this description are herein incorporated by reference in their entirety.

The invention claimed is:

1. A method for improving insulin resistance, which comprises administering an effective amount of a compound represented by formula (I)

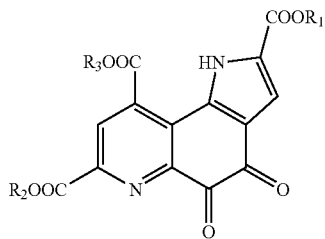

(wherein $R^1$, $R^2$, and $R^3$ independently represent linear or branched $C_{1-6}$ alkyl, linear or branched $C_{2-6}$ alkenyl, linear or branched $C_{2-6}$ alkynyl, aralkyl, araryl, phenyl, or a hydrogen atom) or a salt thereof, to a subject in need of improving insulin resistance.

2. A method for treating type II diabetes, which comprises administering an effective amount of a compound represented by formula (I)

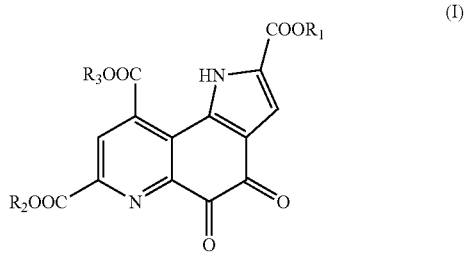

(wherein $R^1$, $R^2$, and $R^3$ independently represent linear or branched $C_{1-6}$ alkyl, linear or branched $C_{2-6}$ alkenyl, linear or branched $C_{2-6}$ alkynyl, aralkyl, araryl, phenyl, or a hydrogen atom) or a salt thereof, to a subject suffering from type II diabetes.

* * * * *